US00PP26356P2

(12) United States Plant Patent
Knosher

(10) Patent No.: US PP26,356 P2
(45) Date of Patent: Jan. 26, 2016

(54) ***GAURA* PLANT NAMED 'LITTLE JANIE'**

(50) Latin Name: *Gaura lindheimeri*
Varietal Denomination: Little Janie

(71) Applicant: Ball Horticultural Company, West Chicago, IL (US)

(72) Inventor: Lynne Knosher, Campton Hills, IL (US)

(73) Assignee: Ball Horticultural Company, West Chicago, IL (US)

( * ) Notice: Subject to any disclaimer, the term of this patent is extended or adjusted under 35 U.S.C. 154(b) by 23 days.

(21) Appl. No.: 14/121,127

(22) Filed: Aug. 4, 2014

(51) Int. Cl.
*A01H 5/02* (2006.01)

(52) U.S. Cl.
USPC ..... Plt./432

(58) Field of Classification Search
USPC ..... Plt./432
CPC ..... A01H 5/02
See application file for complete search history.

*Primary Examiner* — Kent L Bell
(74) *Attorney, Agent, or Firm* — Audrey Charles

(57) ABSTRACT

A new and distinct cultivar of *Gaura* plant named 'Little Janie', characterized by its white and rose bicolored flowers, dark green-colored foliage, and moderately vigorous, upright growth habit, is disclosed.

1 Drawing Sheet

Latin name of genus and species of plant claimed: *Gaura lindheimeri.*

Variety denomination: 'Little Janie'.

BACKGROUND OF THE INVENTION

The present invention relates to a new and distinct cultivar of *Gaura* plant botanically known as *Gaura lindheimeri* and hereinafter referred to by the cultivar name 'Little Janie'.

The new cultivar originated in a controlled breeding program in Elburn, Ill. during June 2005. The objective of the breeding program was the development of *Gaura* cultivars that are free flowering with a more compact growth habit.

The new *Gaura* cultivar is the result of cross-pollination. The female (seed) parent of the new cultivar is the proprietary *Gaura lindheimeri* breeding selection coded 0024-B2-B2, not patented, characterized by its dark rose-colored flowers, dark green-colored foliage, and moderately vigorous, semi-upright growth habit. The male (pollen) parent of the new cultivar is the proprietary *Gaura lindheimeri* breeding selection coded 0032-A1-4, not patented, characterized by its light blush-pink colored flowers, medium green-colored foliage, and moderately vigorous, semi-upright growth habit. The new cultivar was discovered and selected as a single flowering plant within the progeny of the above stated cross-pollination during November 2012 in a controlled environment in Elburn, Ill.

Asexual reproduction of the new cultivar by terminal stem cuttings since November 2012 in Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Little Janie' as a new and distinct cultivar of *Gaura* plant:

1. White and rose bicolored flowers;
2. Dark green-colored foliage; and
3. Moderately vigorous, upright growth habit.

Plants of the new cultivar differ from plants of the female and male parents primarily in flower color.

Of the many commercially available *Gaura* cultivars, the most similar in comparison to the new cultivar is Rosy Jane 'Harrosy', U.S. Plant Pat. No. 22,290. However, in side by side comparisons, plants of the new cultivar differ from plants of 'Harrosy' in at least the following characteristics:

1. Plants of the new cultivar are shorter than plants of 'Harrosy'; and
2. Plants of the new cultivar have darker colored foliage than plants of 'Harrosy'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Little Janie'.

The plants were grown in one-gallon containers for approximately two months in a greenhouse and one month outdoors in Elburn, Ill. Plants were given one pinch prior to transplant and one pinch two weeks after transplant.

DETAILED BOTANICAL DESCRIPTION

Figure 1:
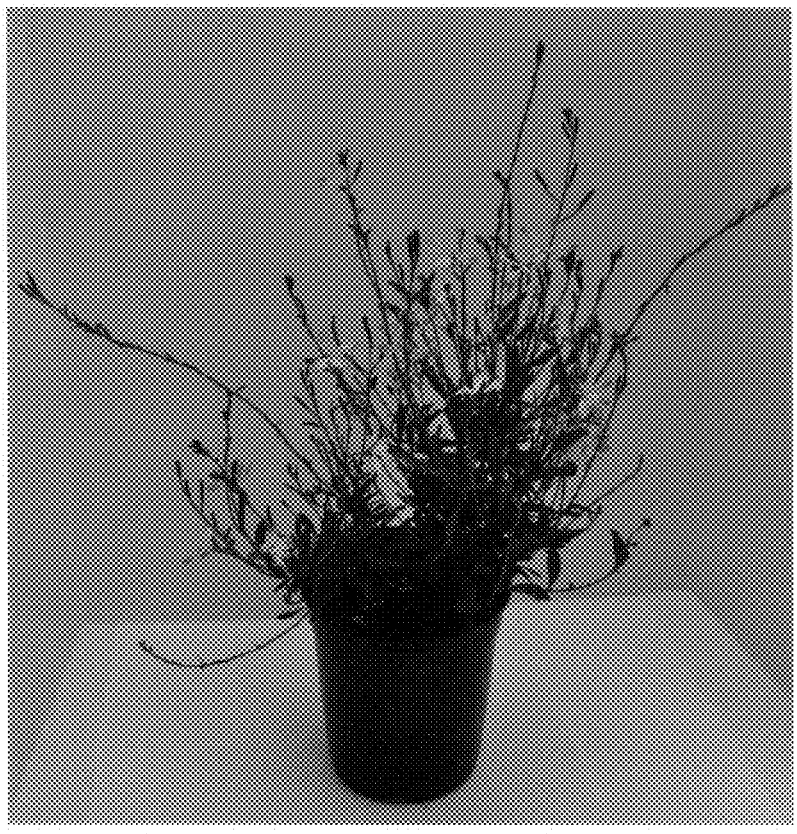
FIG. 1 illustrates a side view of the overall growth and flowering habit of 'Little Janie'.
Figure 2:
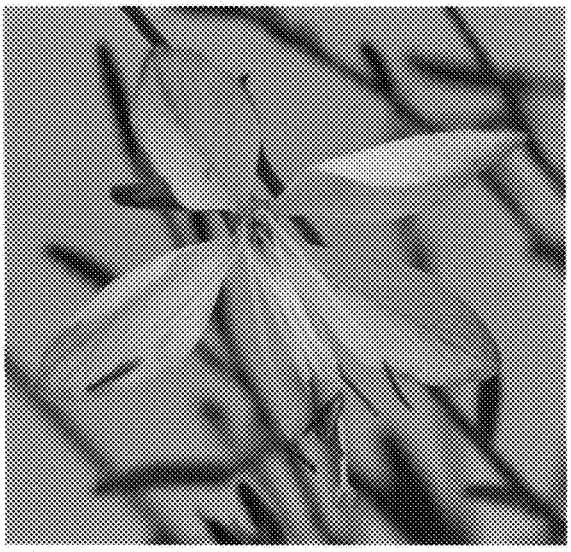
FIG. 2 illustrates a close-up view of an individual flower of 'Little Janie'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in June 2014 under natural light conditions in West Chicago, Ill.

The following descriptions and measurements describe plants produced from cuttings from stock plants and grown under conditions comparable to those used in commercial practice. The plants were grown utilizing a soilless growth medium in one-gallon containers for approximately two months in a greenhouse and one month outdoors in Elburn, Ill. Plants were given one pinch prior to transplant and one pinch two weeks after transplant. Greenhouse temperatures were maintained at approximately 45° F. to 65° F. (7.2° C. to 18.3° C.) during the day and approximately 35° F. to 45° F. (1.7° C. to 7.2° C.) during the night. No supplemental lighting was provided. Measurements and numerical values represent averages of typical plants.

Botanical classification: *Gaura lindheimeri* cultivar Little Janie.

Parentage:

*Female parent*.—Proprietary *Gaura lindheimeri* breeding selection coded 0024-B2-B2, not patented.

*Male parent*.—Proprietary *Gaura lindheimeri* breeding selection coded 0032-A1-4, not patented.

Propagation:

*Type cutting*.—Terminal stem.

*Time to initiate roots*.—Approximately 12 to 14 days.

*Time to produce a rooted cutting*.—Approximately 35 to 42 days.

*Root description*.—Fine, fibrous white to brown in color.

*Rooting habit*.—Freely branching.

Plant description:

*Commercial crop time*.—Approximately 12 to 14 weeks from a rooted cutting to finish in a 15 cm pot.

*Growth habit and general appearance*.—Moderately vigorous, upright.

*Size*.—Height from soil level to top of plant plane: Approximately 45.0 cm. Width: Approximately 50.0 cm.

*Branching habit*.—Freely branching. Pinching enhances lateral branching. Quantity of main branches per plant: Approximately 5.

*Branch*.—Shape: Round in cross section. Strength: Strong, somewhat flexible. Length to base of inflorescence: Approximately 13.5 cm. Diameter: Approximately 3.0 mm. Length of central internode: Approximately 1.1 cm. Texture: Densely pubescent with appressed, soft, short hairs. Color of young stem: 146A. Color of mature stem: 146A often tinted 187B from sun; stems become woody 200C with age.

Foliage description:

*General description*.—Quantity of leaves per main branch: Approximately 8. Fragrance: None detected. Form: Simple. Arrangement: Alternate.

*Leaves*.—Aspect: Perpendicular or acute angle to stem. Shape: Oblanceolate. Margin: Entire to very slightly dentate. Apex: Acute to broadly acute. Base: Attenuate. Venation pattern: Pinnate. Length of mature leaf: Approximately 5.0 cm. Width of mature leaf: Approximately 1.0 cm. Texture of upper and lower surfaces: Densely pubescent with appressed, soft, short hairs. Color of upper surface of young and mature foliage: N137A with venation of 146D. Color of lower surface of young and mature foliage: N137C with venation of 146D.

*Petiole*.—Length: Approximately 4.0 mm. Diameter: Approximately 1.5 mm. Texture: Densely pubescent with appressed, soft, short hairs. Color: 146D.

Flowering description:

*Flowering habit*.—'Little Janie' is freely flowering under outdoor growing conditions with substantially continuous blooming from early spring through autumn.

*Lastingness of individual flower on the plant*.—Approximately 3 to 4 days.

Inflorescence description:

*General description*.—Type: Spicate raceme. Quantity per plant: Approximately 40. Fragrance: None detected. Length or height: Approximately 18.0 cm for most mature. Width: Approximately 6.0 cm. Quantity of fully open flowers per inflorescence: Approximately 1 to 2.

Flower description:

*Type*.—Solitary, actinomorphic, sessile.

*Bud*.—Rate of opening: Generally takes 3 to 4 days for bud to progress from first color to fully open flower.

*Bud just before opening*.—Shape: Oblong. Length: Approximately 1.3 cm. Diameter: Approximately 2.0 mm. Texture: Densely pubescent. Color: 187A to 187B with 137A at tip.

*Corolla*.—Shape: Cruciform. Length: Approximately 3.1 cm. Width: Approximately 3.8 cm.

*Petals*.—Quantity: Four, non-overlapping. Shape: Oblanceolate. Margin: Entire. Apex: Broadly acute to rounded. Base: Attenuate. Length: Approximately 1.8 cm. Width: Approximately 1.0 cm. Texture of upper and lower surfaces: Glabrous. Color of upper surface when first and fully open: NN155D with 71B at apex and feathering toward center. Color of lower surface when first and fully open: NN155D with 71C at apex and feathering toward center.

*Stipule*.—Quantity: 1 per flower. Shape: Lanceolate. Margin: Entire. Apex: Acute. Base: Truncate. Length: Approximately 8.0 mm. Diameter: Approximately 2.0 mm. Color of upper and lower surfaces: 146D with 137A and 187A at apex.

*Calyx*.—Shape: Tubular. Length: Approximately 1.9 cm. Diameter: Approximately 4.0 mm.

*Sepals*.—Quantity per flower: 4, petaloid, fused at tip with tip pointing upward. Shape: Lanceolate. Margin: Entire. Apex: Acute, fused. Base: Truncate. Length: Approximately 1.9 cm. Width: Approximately 2.0 mm. Texture of inner surface: Glabrous. Texture of outer surface: Moderately pubescent. Color of inner and outer surfaces: 187C and 137A with 187A at apex.

*Reproductive organs*.—Androecium: Stamen quantity: 8 per flower, dorsifixed. Stamen length: Approximately 1.5 cm. Filament length: Approximately 1.2 cm. Filament color: NN155D, opaque. Anther shape: Oblong. Anther length: Approximately 3.0 mm. Anther color: 181A, darkens to 187B with age. Pollen amount: Abundant. Pollen color: 4C. Gynoecium: Pistil quantity: 1 per flower, inferior ovary. Pistil length: Approximately 3.7 cm. Stigma shape: Four-lobed. Stigma length: Approximately 1.0 mm. Stigma color: 154D. Style length above hypanthium: Approximately 1.9 cm. Style color: NN155D, opaque. Hypanthium length: Approximately 8.0 mm. Ovary length: Approximately 1.0 cm. Ovary width:

Approximately 2.0 mm. Ovary texture: Moderately pubescent. Ovary color: 146C with an overlay of 187C.

Seed and fruit production: Neither seed nor fruit production has been observed.

Disease and pest resistance: Resistance to pathogens and pests common to *Gaura* has not been observed.

What is claimed is:

1. A new and distinct cultivar of *Gaura* plant named 'Little Janie', substantially as herein shown and described.

* * * * *